(12) United States Patent
Ray

(10) Patent No.: US 9,758,815 B2
(45) Date of Patent: *Sep. 12, 2017

(54) KITS FOR CHARACTERIZATION OF CHROMOSOMAL INVERSIONS USING PROBES

(71) Applicants: KromaTiD, Inc., Fort Collins, CO (US); Colorado State University Research Foundation, Fort Collins, CO (US)

(72) Inventor: F. Andrew Ray, Fort Collins, CO (US)

(73) Assignees: KROMATID, INC., Fort Collins, CO (US); COLORADO STATE UNIVERSITY RESEARCH FOUNDATION, Fort Collins, CO (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/810,008

(22) Filed: Jul. 27, 2015

(65) Prior Publication Data

US 2016/0186247 A1  Jun. 30, 2016

Related U.S. Application Data

(62) Division of application No. 13/270,575, filed on Oct. 11, 2011, now Pat. No. 9,090,935.

(60) Provisional application No. 61/391,949, filed on Oct. 11, 2010.

(51) Int. Cl.
  *C07H 21/04* (2006.01)
  *C12Q 1/68* (2006.01)

(52) U.S. Cl.
  CPC .......... *C12Q 1/6841* (2013.01); *C12Q 1/6827* (2013.01)

(58) Field of Classification Search
  USPC ........................................................ 435/6.11
  See application file for complete search history.

(56) References Cited

U.S. PATENT DOCUMENTS

| | | | |
|---|---|---|---|
| 6,107,030 | A | 8/2000 | Goodwin et al. |
| 6,140,057 | A | 10/2000 | Lucas |
| 6,270,971 | B1 | 8/2001 | Ferguson-Smith et al. |
| 6,828,097 | B1 | 12/2004 | Knoll et al. |
| 7,014,997 | B2 | 3/2006 | Knoll et al. |
| 2002/0081620 | A1 | 6/2002 | Stanton, Jr. |
| 2010/0062434 | A1 | 3/2010 | Bailey et al. |
| 2011/0287425 | A1 | 11/2011 | Ray et al. |

FOREIGN PATENT DOCUMENTS

EP     0 430 402     6/1991

OTHER PUBLICATIONS

U.S. Appl. No. 13/295,585, Nov. 14, 2011, Bailey, et al.
Bailey, et al (1996) "A New Method for Detecting Pericentric Inversions Using COD-FISH" Cytogenetics Cell Genetics 75:248-253.
Bailey, et al (1996) "CO-FISH Reveals Inversions Associated with Isochromosome Formation" Mutagenesis 11(2):139-144.
Bailey, et al (2004) "Strand-Specific Fluorescence in Situ Hybridization: the CO-FISH Family" Cytogenetic and Genome Research 107:14-17.
Jordan, et al (1999) "Detection of Chromosome Aberrations by FISH as a Function of Cell Division Cycle (Harlequin-FISH)" BioTechniques 26:532-534.
Kitts, Paul. (Oct. 2002) "Genome Assembly and Annotation Process." Database [Online] The NCBI Handbook Part 2. Data Flow and Processing, 1-2. Available Website: www.ncbi.nlm.nih.gov/books/bv.fcgi?rid=handbook.chapter.ch14 Last Update: Aug. 2003 Accessed on: Aug. 8, 2007.
NCBI Genomic Biology "AGP File Specification" Database [Online] 1(1), 1-4. Available Website: www.ncbi.nlm.nih.gov/genome/guide/Assembly/AGP_Specification.shtml Last Update: Oct. 2006 Accessed on Aug. 8, 2007.
NCBI Genomic Biology "Annotation Information" Database [Online] 1-4. Available Website: www.ncibi.nlm.nih.gov/genome/guide/build.html Last Update: Oct. 2006 Accessed on: Aug. 8, 2007.
NCBI Genome Biology "Assembly Information" Database [Online] 1-4. Available Website: www.ncbi.nlm.nih.gov/genome/guide/Assembly/Assembly.shtml Last Update: Oct. 2006 Accessed on: Aug. 8, 2007.
Ray, et al. (2011) "Detecting Chromosomal Inversions Using Chromatid Paints—Potential Use for Retrospective Biodosimetry" International Biodosimetry Research Symposium, Bethesda, MD (Abstract).
Wojcik, et al (1999) "Analysis of Inversions and Sister Chromatid Exchanges in Chromosome 3 of Human Lymphocytes Exposed to X-rays" Mutagenesis 14(6):633-637.

*Primary Examiner* — Kenneth Horlick
(74) *Attorney, Agent, or Firm* — Swanson & Bratschun, L.L.C.

(57) ABSTRACT

A kit for the characterization of chromosomal inversions using single-stranded probes that are either all identical or all complementary to a single-stranded chromatid is described. Reporter species are attached to oligonucleotide strands designed such that they may hybridize to portions of only one of a pair of single-stranded sister chromatids which may be prepared by the CO-FISH procedure. If an inversion has occurred, these marker probes will be detected on the second sister chromatid at the same location as the inversion on the first chromatid. The kit includes non-repetitive probes that are either all identical or all complementary to at least a portion of a target DNA sequence of only one DNA strand of only one chromatid and may in some embodiments include reagents suitable for performing CO-FISH and/or reagents for hybridizing the probes to the target DNA sequence.

8 Claims, 3 Drawing Sheets

KITS FOR CHARACTERIZATION OF CHROMOSOMAL INVERSIONS USING PROBES

RELATED APPLICATION

This application is a divisional application of U.S. application Ser. No. 13/270,575, filed Oct. 11, 2011, which will issue as U.S. Pat. No. 9,090,935 on Jul. 28, 2015, which claims the benefit of U.S. Provisional Application Ser. No. 61/391,949, filed Oct. 11, 2010, each of which is incorporated herein by reference in its entirety.

This invention was made with government support under Grant No. NNX09CE42P awarded by NASA. The government has certain rights in the invention.

FIELD OF THE INVENTION

The present invention relates generally to detection of chromosomal aberrations and, more particularly, to chromosome-specific chromatid painting for detection of inversions.

BACKGROUND OF THE INVENTION

Analysis of cancer cells has led to the discovery of more than 500 tumor-specific chromosome aberrations. Detailed analysis of the breakpoints involved in these structural chromosomal rearrangements has been instrumental in the discovery of many cancer-related genes. Of all possible types of structural chromosome anomalies, inversions, which represent a reversal of orientation of a DNA segment within a chromosome, are found comparatively rarely among the known tumor-specific aberrations. Inversions can have genetic effects similar to the easily detected translocations between different chromosomes seen in cancer. Both can result in effects such as disrupting regulatory sequences that control gene expression or creating genetic rearrangements like gene fusions. Inversions form through the same mechanism as translocations, the misrepair of DNA double-strand breaks. Thus, it might be expected that translocations and inversions should be found in comparable numbers. One possible explanation for the discrepancy is that standard karyotype analyses are relatively insensitive to the detection of inversions and consequently have largely failed to find many tumor-specific chromosome aberrations of this type.

New approaches to measuring incorrect rejoining of radiation-induced DNA double-strand breaks in human cells has led to the conclusion that radiation produces at least ten times the number of chromosomal rearrangements than can now be observed cytogenetically, the vast majority of which are intra-chromosomal (that is, small interstitial deletions and inversions). To the extent that radiation is representative of other mechanisms of creating inversions, it appears likely that their significance has been underestimated and underappreciated in many diseases in addition to cancer.

In addition to cancer cytogenetics (the study of chromosomes and how changes in chromosome structure and number can lead to the loss of regulation and control of cell proliferation, and orderly differentiation of cells in tissues), chromosome analysis is widely used in prenatal screening as well as the diagnosis of congenital abnormalities, learning difficulties, impaired fertility, and sexual development problems.

The two methods frequently used for detection of gross cytogenetic aberrations such as translocations are whole chromosome painting by fluorescence in situ hybridization (FISH), and G- or R-banding. The sequence does not have to be known for either technique. Both chromatids of a chromosome are indiscriminately targeted by these techniques. Whole-chromosome-specific-FISH painting consists of using DNA, highly enriched for sequences unique to a particular chromosome, labeled with a reporter molecule, such as a fluorochrome, and hybridizing it to metaphase chromosome spreads. At the same time, hybridization of any labeled repetitive sequences (common to all chromosomes) that may be present is blocked by competitive hybridization to unlabeled repetitive DNA. In this manner, stable aberrations such as translocations can be observed. FISH and the combinatorial derivatives of FISH, such as Spectral Karyotyping, are generally limited by their ability to detect only breaks, interchanges and numerical aberrations. Giemsa-banding, also known as G-banding, or similar approaches such as R- or Q-banding, is suitable only for detecting changes in banding patterns caused by chromosome inversions when the inversion involves a segment of the chromosome large enough to produce a recognizable change in the pattern of banding. While it may be possible with difficulty to detect an inversion with breakpoints near the midpoints of adjacent dark and light bands, many larger disruptions involving regions containing more than two or three bands might not always produce a recognizable change in these light/dark patterns of banding. Band lengths of fully condensed human mitotic chromosomes average ~$10^7$ base pairs.

A chromatid is a replicated chromosome consisting of two identical parts that will be divided equally between daughter cells at mitoses when two new cells are created from one as cell populations grow. At mitosis, then, each chromosome consists of two identical chromatids and each of these consists of a linear, double-stranded DNA molecule. A strand of DNA is basically a phosphate deoxyribose polymer, each with one of four purine or pyrimidine base residues (A, T, G, or C) attached. Beginning with the first sugar there is a phosphate group at the 5' position and a hydroxyl group at the 3' position. This hydroxyl group is in turn joined to the next sugar at the 5' position and the alternating chain continues until the other end of the linear strand where there is a 3' hydroxyl group. The strands are associated by hydrogen bonding and are thus not covalently joined. The hydrogen bonding between the two strands occurs only between certain bases; that is, A with T and C with G. This results in what is known as complementary base pairing between the two opposite strands.

The genome of a cell must be replicated prior to the process of cell division in order to provide the same genetic information contained in the parent cell to each of the two new daughter cells. Before this replication, each chromosome consists of one double stranded DNA molecule, with one strand complementary to the other. During replication the complementary single strands of the chromosome are effectively separated, with each one becoming the basic part of a new chromatid. If one of these parental strands is oriented in the 5'→3' direction along its length with respect to some arbitrary reference direction, then the 5'→3' direction of the complementary strand will be oriented in the opposite direction. After replication the new synthesized strands each will likewise be complementary to its respective parental strand. The 5'→3' direction of single strands within a double stranded DNA molecule is sometimes referred to as the polarity of the strand.

An inversion is an abnormality in chromosome structure that can result from, effectively, two double-stranded breaks occurring at different points along a portion of the chromosome, and rather than the breaks becoming rejoined in their original condition by cellular DNA repair processes, they occasionally rejoin incorrectly in such a way that this interstitial portion of the chromosome becomes effectively rotated through 180° after a "misrejoining" among the broken ends. Importantly, this misrejoining must occur in such a way as to maintain the same 5'→3' polarity of the strands of the chromosome and that of the inverted segment. While the backbone polarity is maintained, the DNA sequence of the nitrogenous bases within the segment is reversed.

Chromosome 'paints' are mixtures of fluorescent DNA probes, or other types of molecular markers, highly enriched in sequences unique to a particular chromosome that allow a specific chromosome to be identified based on accepted cytogenetic practices that render the chromosome visible using a fluorescent microscope. Such probes can be purchased from a number of vendors.

The first complete draft of the human genome was made in 2000, and refinements have been made to the database since then. The GenBank database is made available to the public by the National Center for Biotechnology Information (NCBI) of the National Library of Medicine of the National Institutes of Health. Most of the DNA sequences have been ordered into contiguous sequences called contigs.

The CO-FISH technique, developed in the 1990s, permits fluorescent probes to be specifically targeted to sites on either chromatid, but not both. To date, this technique has been used almost entirely for detection of highly repetitive DNA which consists of a series of DNA sequences repeated over and over again, up to thousands of times and which contains few, if any, genes. Such regions are commonly found at sites on a chromosome involved in the mechanics of genome partitioning such as centromeres and telomeres. In "Strand-Specific Fluorescence in situ Hybridization: The CO-FISH Family" by S. M. Bailey et al., Cytogenet. Genome Res. 107: 11-14 (2004), chromosome organization is studied using strand-specific FISH (fluorescent or fluorescence in situ hybridization) [CO-FISH; Chromosome Orientation-FISH] which involves removal of newly replicated strands from the DNA of metaphase (mitotic) chromosomes, resulting in single-stranded target DNA. Each newly replicated double helix contains one parental DNA strand plus a newly synthesized strand, and it is this newly synthesized strand that is removed. When labeled single-stranded probes are hybridized to such targets, the resulting strand-specific hybridization is capable of providing previously unattainable cytogenetic information. Hybridization is a process in which two complementary nucleic acid sequences anneal by base pairing. In the context of FISH, "in situ" refers to hybridization of a nucleic acid sequence probe to the DNA of chromosomes, where the chromosomes are in cells that are attached to a glass microscope slide.

For example, it is known that mammalian telomeric DNA consists of tandem repeats of the (TTAGGG) sequence, oriented 5' to 3' towards the termini of all vertebrate chromosomes. Thus, CO-FISH with a suitable telomere probe reveals the absolute 5' to 3' orientation of DNA sequences relative to the chromosome's pter→qter direction (end of p or short arm of the chromosome to the end of the q or long arm of the chromosome).

The removal of the newly replicated strands using the CO-FISH procedure leaves the original (parental) strands largely intact. Thus, for the purposes of subsequent hybridization reactions, the two sister chromatids of a chromosome are rendered single stranded, and complementary to one another. The ability of CO-FISH to restrict hybridization of single-stranded probes to only one of the two sister chromatids means that it can also be used for inversion detection. Because an inversion reverses the orientation of the DNA sequences within the inversion region, it becomes visible as a jump or switch in probe signal from one chromatid to its sister chromatid. Such a switch can readily be detected when compared to a reference probe outside of the inverted region.

SUMMARY OF THE INVENTION

Therefore, it is an object of the present invention to provide a sensitive method for the detection of chromosomal inversions.

Still another object of the invention is to provide a probe kit for the sensitive detection of chromosomal inversions.

Additional objects, advantages and novel features of the invention will be set forth in part in the description which follows, and in part will become apparent to those skilled in the art upon examination of the following or may be learned by practice of the invention. The objects and advantages of the invention may be realized and attained by means of the instrumentalities and combinations particularly pointed out in the appended claims.

To achieve the foregoing and other objects, and in accordance with the purposes of the present invention, as embodied and broadly described herein, the method for detecting inversions in a selected mitotic chromosome, hereof, includes the steps of: generating a pair of single-stranded sister chromatids from said selected chromosome, each sister chromatid having a length of DNA and a series of target DNA sequences that span a portion of the length of the DNA of the chromatid; generating a plurality of non-repetitive probes, wherein each of the probes is single-stranded, unique and identical to at least a portion of a target DNA sequence, each of the probes having at least one label, thereby permitting detection thereof; hybridizing the probes to the sister chromatids; and detecting the hybridized probes; whereby if no inversion exists, all of the probes will hybridize to one of the sister chromatids, and whereby if an inversion exists, at least one of the probes will hybridize to the other sister chromatid at the same location as the inversion.

In another aspect of the present invention and in accordance with its objects and purposes, the method for detecting inversions in a selected mitotic chromosome, hereof, includes the steps of: generating a pair of single-stranded sister chromatids from said selected chromosome, each sister chromatid having a length of DNA and a series of target DNA sequences that span a portion of the length of the DNA of the chromatid; generating a plurality of non-repetitive probes, wherein each of the probes is single-stranded, unique and complementary to at least a portion of a target DNA sequence, each of the probes having at least one label, thereby permitting detection thereof; hybridizing the probes to the sister chromatids; and detecting the hybridized probes; whereby if no inversion exists, all of the probes will hybridize to one of the sister chromatids, and whereby if an inversion exists, at least one of the probes will hybridize to the other sister chromatid at the same location as the inversion.

In yet another aspect of the present invention and in accordance with its objects and purposes, the kit for detecting inversions in a selected mitotic chromosome, hereof, includes a plurality of non-repetitive probes, wherein each of the probes in the plurality of probes is single-stranded, unique and identical to at least a portion of a target DNA sequence of a chromatid of the chromosome, each of the probes having at least one label, thereby permitting detection thereof.

In still another aspect of the present invention and in accordance with its objects and purposes, the kit for detecting inversions in a selected mitotic chromosome, hereof, includes a plurality of non-repetitive probes, wherein each of the probes in the plurality of probes is single-stranded, unique and complementary to at least a portion of a target DNA sequence of a chromatid of the chromosome, each of the probes having at least one label, thereby permitting detection thereof.

Benefits and advantages of the present invention include, but are not limited to, providing a sensitive method for detecting chromosomal inversions.

BRIEF DESCRIPTION OF THE DRAWINGS

The accompanying drawings, which are incorporated in and form a part of the specification, illustrate an embodiment of the present invention and, together with the description, serve to explain the principles of the invention. In the drawings:

FIG. 1A is a schematic representation of an embodiment of the present method where one DNA strand of each chromatid in a chromosome is removed using the CO-FISH or another procedure, and one of the two resulting single-stranded chromatids is painted, while

DETAILED DESCRIPTION OF THE INVENTION

Figure 1A:
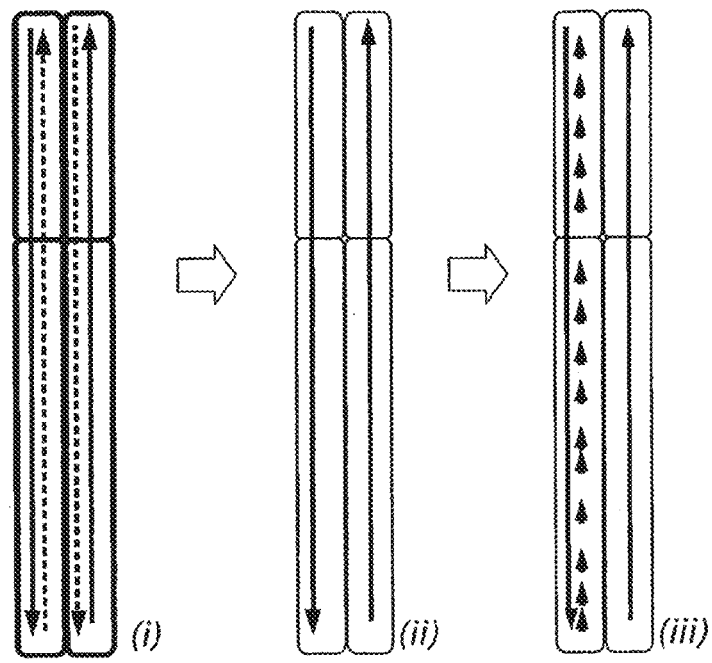

Briefly, the present invention includes a method for detecting inversions in chromosomes using hybridizing probes for painting one chromatid in order to refine the process of chromosome painting to generate additional information; that is, instead of painting an entire chromosome, probes are developed for painting either chromatid.

If the 5'→3' base ordering of either of the sister chromatids is known, the DNA sequence for the sister chromatid can be determined since the sequences are complementary and therefore different in terms of annealing (hydrogen bonding process, also known as base pairing) to fluorescent or other marker probes. The paint on one chromatid technique of the present invention uses CO-FISH (See, e.g., S. M. Bailey et al, supra.) to destroy newly replicated strands in both chromatids. It differs from existing CO-FISH technology in that its object is to hybridize multiple probes to a chromatid so as to give the visual impression upon detection of having painted a large portion of the entire chromatid. This may be accomplished by selecting unique DNA sequences, such as are often found in the exons of genes, for use as probes. Genome databases provide large segments of contiguous DNA sequences that can be investigated for suitability as directional targets/probes, and provide a mechanism for determining orientation relative to other targets/probes and for checking these sequences for uniqueness (occurring once in the genome) by performing what is known as a blast n (blast) search.

An embodiment of the method of the present invention is performed as follows:

(1) Large, contiguous DNA sequences (contigs) that are unique to specific chosen chromosomes and therefore to the chromatids to be used as targets, from which probes are designed, are identified using genomic databases.

(2) These sequences are checked for uniqueness (presence only on one specific chromatid), by performing a blast search, which defines the nucleotide sequence database. Both the actual sequences as input, and their complements are compared to the entire genomic database point-for-point, base-by-base, and matching sequences are returned in order of their percentage homology, from highest to lowest; that is, completely-matched sequences located on alternate chromosomes in the same genome are identified and eliminated.

(3) Analysis of database to determine adequacy of coverage which is defined as the ability of a fluorescent probe set to completely cover a specified chromatid from end to end. Full (100%) coverage would be hybridization to every base, but is clearly not useful for the present method because there are many sequences that are not unique in a chromosome. It is believed by the inventors that the coverage of chromosome-specific unique sequences will allow coverage of unique target sequences where detectable probes are spaced at 1 Mbp intervals along the length of the chromatids, excluding large repetitive regions such as centromeres and telomeres. Coverage of gene-rich regions may be increased in other embodiments of the invention.

(4) Synthesizing and labeling suitable probes, as will be described in detail in the EXAMPLES.

(5) Generating single-stranded sister chromatids in accordance with CO-FISH or another suitable procedure (See, e.g., S. M. Bailey et al., supra, and U.S. Pat. No. 6,107,030 for "Determining Orientation And Direction Of DNA Sequences" which issued to Edwin H. Goodwin and Julianne Meyne on Aug. 22, 2000, the teachings of which patent are hereby incorporated by reference herein.).

(6) Hybridizing the single-stranded probes to the single-stranded chromatids, as will be described in the EXAMPLES.

(7) Detecting the single-stranded fluorescent probes hybridized to one chromatid and not the other. Detection of such probes hybridized to chromosome 19p has been achieved. Although high background was observed, probe hybridization appears to be specific.

(8) Developing chromatid paints (mixtures of probes complementary to the same chromatid), as will be described in the EXAMPLES.

Reference will now be made in detail to the present embodiments of the invention, examples of which are illustrated in the accompanying drawings. In the FIGURE, similar structure will be identified using identical reference characters. A metaphase chromosome consists of 2 linear, double-stranded DNA molecules. This form of the DNA is a packaging mechanism that is used to distribute two identical copies of the DNA molecule during cell division. Turning now to FIG. 1A, a schematic representation of one embodiment of the present method is illustrated. Chromosome (i) shows the untouched chromosome after replication, while chromosome (ii) illustrates the newly replicated DNA strand of each chromatid in the chromosome having been removed using CO-FISH or another procedure, leaving the separated parental chromatid strands oriented in opposite directions.

Chromosome (iii) shows the resulting chromatids after having been exposed to the directional probes of the present invention described hereinbelow, and illustrates the situation where there are no detectable inversions present since upon investigation with a fluorescent microscope in the case of fluorescent probes having been used, no probes appear on the second chromatid.

Figure 1B:
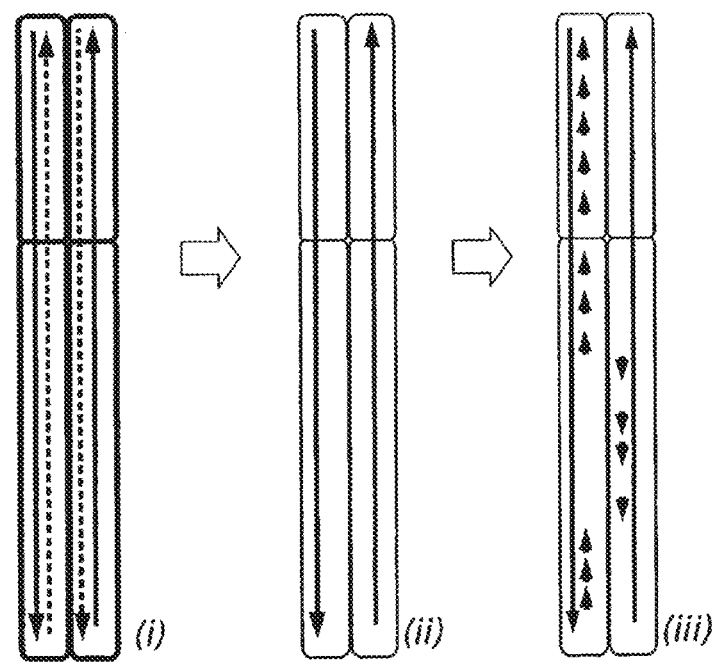
FIG. 1B is a schematic representation illustrating the same procedure as described in FIG. 1A hereof, but for a chromosome having an inversion.

FIG. 1B is a schematic representation illustrating the same procedure as described in FIG. 1A hereof, but for a chromosome having an inversion. It should be mentioned that the identical chromatid probe mixture would be used to generate the results in both FIGS. 1A and 1B. As may be observed from FIG. 1B, the molecules are not identical in the newly replicated DNA strands; that is, there is an inversion present which is not observed in chromosomes (i) and (ii) until the chromatids are painted using the directional probes of the present invention and examined using a fluorescent microscope, as an example, when fluorescent probes have been used [chromosome (iii)]. The inverted portion of the first chromatid is not painted, while only the complementary portion appears on the second chromatid as a painted section and is portrayed in the opposite (inverted orientation) by the arrowheads.

Synthetic oligomers (oligonucleotides, or oligos), are widely used as probes in molecular biology and cytogenetics. In cytogenetic research, a probe allows the chromosomal locations of DNA target sequences to be determined. An oligomer is a single strand of DNA, RNA or PNA (peptide nucleic acid). To generate probes, a label must be attached to the oligomer. For use in chromosome analysis, the label is often a fluorescent molecule in order that the probe can be visualized using fluorescence microscopy. A common labeling procedure utilizes an enzyme called terminal deoxynucleotidal transferase, also known as terminal transferase. This enzyme is a template-independent DNA polymerase that adds deoxynucleotides to the 3' end of DNA oligomers. To label a probe, a polymerization reaction is prepared with terminal transferase, the oligomer, and a deoxynucleotide triphosphate that has a fluorophore (fluorescent molecule) coupled to it. During the polymerization reaction, terminal transferase adds one or more fluorescently labeled deoxynucleotides to the 3' end of the oligomer.

Oligos can also be labeled directly during commercial synthesis on either their 5' or 3' ends with fluorescent molecules, fluorescent particles or molecules such as biotin which are readily detectable using secondary reagents such as avidin to which a fluorescent molecule has been attached.

Another embodiment in accordance with the present invention is use of complementary or anti-parallel probe(s) that anneal to the opposite chromatid from the chromatid being painted. These complementary probe(s) are designed to anneal to the opposite chromatid, but unlike the previous embodiments, the probe intentionally appears on the opposite chromatid—in the absence of an inversion; i.e., the anti-parallel probe is designed to anneal to the opposite chromatid from the painted chromatid. These complementary probes therefore, in effect, simulate the pattern of an inversion in the absence of a true inversion.

Figure 2:
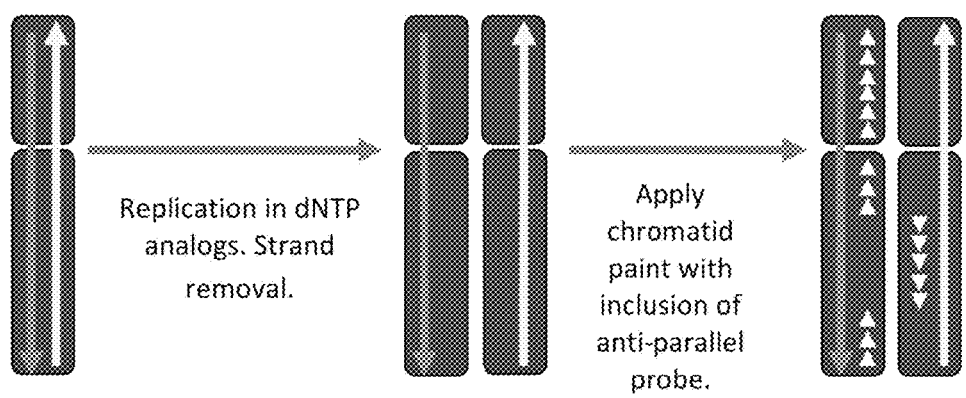
FIG. 2 is a schematic representation of an embodiment of the present method where one or more probes used to paint a chromatid is replaced by one or more probes having an anti-parallel orientation to that probe, the anti-parallel probe designed to anneal to the other or opposite chromatid and be used as a reference point for embodiments herein.

Referring to FIG. 2, probes are prepared as previously described herein to selectively paint a specific chromatid. However, one (or more) of the probe sets is replaced with the anti-parallel (complimentary) sequences. The predicted pattern, showing anti-parallel probe sets hydribized to the opposite chromatid, is shown. The location and size of the anti-parallel probe set(s) is known and therefore it serves as a reference point along the chromatid.

Simulating inversions has provided utility by: (1) verifying that a single probe set can hybridize to the other (opposite) chromatid (in essence appearing as an inversion) and illustrating that embodiments of this invention can be used to detect/confirm small inversions with a high degree of accuracy (>90%); (2) the complementary probe(s) can be used to anneal to the opposite chromatid thereby proving that inversions as small as 1 Mb can be detected using the embodiments described herein (illustrating the high resolution of embodiments herein); (3), the complementary probe(s) also act as a reference point along the chromatid, since the location and size of the "pseudo-inversion" are known, information relevant to establishing a landmark along the chromatid. The landmark gives both location (where are you along the chromatid) and size (how big is an inversion) for use in resolving inversion detection. And, (4) the complementary probe(s) can be used as a standard for quantitative measurements (size and/or length) by providing a defined number of probes in the context of invention.

In one embodiment of the complementary probe embodiment, complementary probe sets are developed from known probe sets to a particular chromatid (as described previously) by simply using the complimentary sequence of the original probe and designing probe set(s) having anti-parallel orientation. This makes the complementary probe set(s) anti-parallel to the original paint probe (thereby recognizing and annealing to the same location as the original probe, but on the sister chromatid). The anti-parallel probes replace their complementary sequences in the original paint probe cocktail (described in the methods above), and are used in combination with the other original probes, e.g., anti-parallel probes can be developed every 10 Mb to 100 Mb along the chromatid, etc. In one embodiment an anti-parallel probe is developed to be spaced along a chromatid every 100 Mb and in some embodiments every 10 Mb. In some embodiments the complementary probes are labeled with a different color fluorescent label to provide additional resolution to the visualization of the pseudo-invention. The location and size of the anti-parallel probe set(s) are known and can be used in conjunction with chromatid painting to provide reference for measuring actual inversions.

Having generally described the invention, the following EXAMPLES provide additional detail:

Example 1

Selection of Sequences

As stated hereinabove, identification of large contiguous DNA sequences (contigs) that are unique to specific chromosomes to be used as targets is achieved by database analysis of publicly available genomic DNA sequences. Within these contigs, shorter sequences ~40-50 bases long were selected for use as probes and then checked for uniqueness to one specific chromatid by performing a blast search. Sequences 20-90 bases long are anticipated to be useful in the practice of the present invention. Commercially available software programs such as Array Designer are linked to this database function.

The database is analyzed to determine the ability of a fluorescent probe set to cover a specified chromatid. It is believed by the inventors that coverage of chromosome-specific unique sequences using detectable probes spaced at 1 Mbp intervals along the length of the chromatids, excluding large repetitive regions such as centromeres and telomeres should be adequate to detect a large number of heretofore undetectable inversions. Increased coverage is expected to improve detection.

Example 2

Preparation of Probes
1. Generating Sequence Specific DNA:
   (a) By PCR:
   Sequence-specific genomic DNA suitable for locus-specific probes was obtained by amplifying specific targets in the genome using PCR. It should be pointed out that DNA complementary to the specific targets may also be used. The size of the PCR product was specified from 7.5 to 9.5 kbp. Primer pairs separated by the desired target size were generated by using 10 kbp DNA sequence segments at approximately 1 Mbp intervals. As primers were identified they were verified using blast (GenBank) to assure that the primer sequence was unique to chromosome 19p. Primer sequences found to anneal to additional human chromosomes were excluded from further consideration. If no primer pairs resulted from a 10 kbp sequence, then the next contiguous 10 kbp was screened.
   Microgram quantities of pure genomic DNA were prepared from normal human fibroblasts using Qiagen's DNAeasy columns according to manufacturer's recommendations. Polymerase Chain Reaction (PCR) was performed using Stratagene EXL polymerase. The PCR product was examined by gel electrophoresis, and if multiple bands were observed PCR was repeated with upward annealing temperature adjustments until a single band was obtained. PCR products of the expected size were routinely obtained using EXL polymerase, with several micrograms of PCR product being routinely produced. The PCR products are the size predicted by genome analysis.
   (b) By Oligo Tiling and Commercial Synthesis:
   Array designer 4 software from PREMIER Biosoft International was used to develop a tiled array covering exon 3 of the mucin gene located on chromosome 19p. For the present purpose, a tiled array is defined as a series of ordered, short, individual DNA sequences that are complementary to a corresponding larger contiguous target DNA sequence. The program provides a number of variable parameters. The exon DNA sequence was copied from the NCBI database, pasted into the software, and queried to produce a tiled array. The array consisted of a series of non-overlapping sequences, each 48-52 nucleotides long that were separated by 5 intervening bases. The software checked all sequences for homology elsewhere in the genome using a built in blast search function. 189 oligos were prepared by a commercial vendor. The probe regions corresponded to tiled sequences identified by Array Designer, and was chosen to cover about 10 kbp.
2. Labeling Probes:
   (a) PCR:
   Four of the chromosome 19-specific PCR products were chosen for linear DNA amplification. These were at 1 Mbp intervals starting at 1 Mbp from the end of the 19p chromosome. Approximately 0.5 µg PCR DNA was used for the linear DNA amplification template. The templates that will be used to cerate probes using the linear amplification process are the double-stranded PCR products that were chosen from the genomic database to be spaced at 1 Mbp intervals along the chromosome. These four products, although separated by great distances on the chromosomes can be oriented 5'→3' based on the information from the genome database that they are all in the same contig. In order to generate a probe to one parental strand and not the other, primers were chosen that were from the same parental strand. In actual practice this was done during primer design, those primers designated as forward primers were all on the same strand with respect to a given contig sequence, and reverse primers were all on the complementary strand. Only single primers were used in linear DNA amplification reactions to produce labeled single-stranded DNA probes. The DNA amplification conditions were virtually identical to PCR conditions using genomic DNA in which the PCR template was synthesized except that the reactions now contained AlexaFluor 594-5-dUTP in an approximately 1:4 molar ratio with dTTP. In side-by-side comparisons of linear DNA amplification reactions with or without labeled nucleotides, similar bands were obtained on electrophoretic gels and similar amounts were determined spectrophometrically. The yield of these reactions has reproducibly been several micrograms. It should be mentioned that other labeled nucleotides may also be used to prepare the probes of the present invention.
   An 8.5 kbp PCR product was used as a template for linear DNA amplification. Only single primers were used. For FISH, probe lengths of 300-500 bases have been shown to produce better results than longer or shorter probes. Commercially available Hae III is a restriction endonuclease having a four by recognition sequence that on average cuts once every 256 bp, and has been reported to digest both single-stranded and double stranded DNA (See, e.g., Reference 1.). It has been found that Hae III not only cuts single-stranded DNA, but reduces it to the desired size for FISH.
   (b) Using Terminal Transferase:
   This procedure labels 35 picomoles of single-stranded oligomer using the enzyme terminal transferase to add one or more fluorescent nucleotides to the 3' ends of the oligomer molecules. The oligomer typically is single-stranded DNA that has been made synthetically such that it has a sequence complementary to the chromosomal sequence we wish to detect. An example of a labeling reaction is as follows: The dry as purchased oligomer was dissolved in distilled water. A reaction mixture is prepared consisting of distilled water sufficient to give a final volume of 20 microliters, concentrated reaction buffer to give a 1× final concentration, and 35 pico moles of oligomer. To this reaction mixture are added 2.5 mM $CoCl_2$, 0.1 mM fluorescently labeled nucleotide triphosphate, and 50 units of terminal transferase, or other suitable enzyme, where the amounts given are final concentrations and can be adjusted to give satisfactory results. The reaction mixture is incubated at 37° C. for a period of time typically 7 to 9 min. 25 mM of EDTA is added to stop the reaction immediately after 7-9 min. of incubation and the volume is adjusted to 100 microliters by adding distilled water.

Example 3

CO-FISH Using Probes Generated by PCR
CO-FISH have been described in detail previously, and was used here with some modification. Primary human dermal fibroblasts (catalog #C-004-5C, sold by Cascade Biologics) were subcultured into medium containing 5-bromo-2'-deoxyuridine (Sigma) at a final concentration of $10^{-5}$ M and collected ~24 hours later (one cell cycle). Colcemid (0.1 µg/ml; Gibco) was added for the final four hours to accumulate mitotic cells. Cultures were trypsinized (Trypsin-EDTA; Gibco) and cells suspended in 75 mM KCl hypotonic solution at 37° C. for 15 min. before fixation in fresh 3:1 methanol/acetic acid. Fixed cells were dropped onto cold, wet glass microscope slides and allowed to dry slowly in a humid environment.

Prior to hybridization of the labeled, single-stranded 19p oligomer probe cocktails, slides were aged and treated with 0.5 mg/ml RNase A for 10 min at 37° C. [5], then stained with 0.5 µg/ml Hoechst 33258 (Sigma) in 2×SSC (saline sodium citrate; 1×SSC is 0.15 M NaCl, 0.015 M sodium citrate) for 15 min. at room temperature. Slides were then exposed to 365-nm UV light generated by a Stratalinker 1800 UV irradiator for 25-30 min. Enzymatic digestion of the BrdU-substituted DNA strands with 3 U/µl (U?) of Exonuclease III (Promega) in buffer supplied by the manufacturer (50 mM Tris-HCl, 5 mM $MgCl_2$, and 5 mM dithiothreitol, pH 8.0) was allowed to proceed for 10 min at room temperature. An additional denaturation in 70% formamide, 2×SSC at 70° C. for various times was performed, followed by dehydration in a cold ethanol series (70%, 85%, 100%).

Example 4

Hybridization

A probe hybridization mixture containing 50% formamide, 10% 2×SSC and 10% dextran sulfate, 1% COT1 DNA to block repetitive sequences, and labeled, single-stranded pooled probe [~100 ng each] was denatured at 65° C. for 1 min. and applied to slides prepared for CO-FISH (as above). Following an overnight hybridization at 37° C. in a moist chamber, slides were washed at 42° C., three minutes each, in: 1) 50% formamide/2×SSC (two washes); 2) 2×SSC (two washes); 3) PN Buffer (Phosphate NP-40); and 4) PN Buffer at room temperature for 5 min., then mounted in a glycerol solution containing 1 mg/ml of the antifade compound p-phenylenediamine HC; and 0.1 µg/ml 4',6-diamidino-2-phenylindole (DAPI). It should be mentioned that when probes are generated by the PCR method described hereinabove, inevitably there are repetitive sequences in them. Such sequences are labeled and bind to multiple places on many chromosomes which is undesirable. COT 1 DNA is composed of unlabeled DNA from repetitive sequences. During hybridization, COT 1 DNA competes with and, in effect, blocks hybridization from the labeled repetitive sequences in the probe.

Example 5

Detection

Individual metaphase spreads are examined with a fluorescence microscope and images captured using a CCD camera. On selected slides, a direct-labeled (FITC), a 19q arm-specific DNA paint probe was hybridized as per manufacturer's instructions (Q-BIOgene) to verify that probes were in fact hybridizing to chromosome 19.

Example 6

Results

Using both strategies to produce probes, PCR and tiled oligos produced similar results. Red fluorescence from chromosome 19 was observed on single chromatids using an epifluorescent microscope. Although there was significant background signal associated with other chromosomes, the presence of the signal confirmed that the probes had incorporated at least one molecule of AlexaFluor 594-5 dUTP, and were capable of being detected. It is expected that non-specific background staining can be reduced by increasing the stringency of hybridization and adding subsequent wash steps. Other fluorescent or non-fluorescent labels, either singly or in combination, may be incorporated into probes using the same methodology.

Example 7

Generation of Paints

Developing paints is achieved by performing the same operation multiple times along the length of a contig at the stated 1 Mbp interval and then increasing the coverage as desired. Adjacent contigs have an information gap between them. In the databases the contigs are presented with a hypothesized orientation. In order to develop a chromatid paint these orientations must be confirmed. Therefore when probes have been developed for two adjacent contigs, they will be labeled with different fluorochromes. Metaphase chromosomes from multiple normal individuals will be used for CO-FISH. If the two colors are found on the same chromatid in all individuals, the database is correct and assembly of the paint components can continue. If the colors are found on opposite chromosomes from all individuals, the orientation of the contig is reversed from its published orientation. If this is the situation, a new probe set may be prepared using sequences complementary to the unique sequences chosen previously, and paint assembly can continue again with the correctly oriented probes.

The visual effect of a chromatid paint is to make the two sister chromatids of a mitotic chromosome appear different, and distinguishable, from one another. As an example, the probes of a chromatid paint might be labeled with fluorescein, a green-fluorescing dye, and total DNA stained with propidium iodide, a red-fluorescing DNA-binding dye. In this case, one chromatid would fluoresce red and the other yellow (green plus red appears yellow). If the chromatid paint is applied to a chromosome that has an inversion, label within the inverted region appears on the opposite chromatid producing a distinctive pattern.

Example 8

Demonstration of Increased Detection Resolution Using "Mini-Paint" Using "Pseudo-Inversion"

Figure 3:
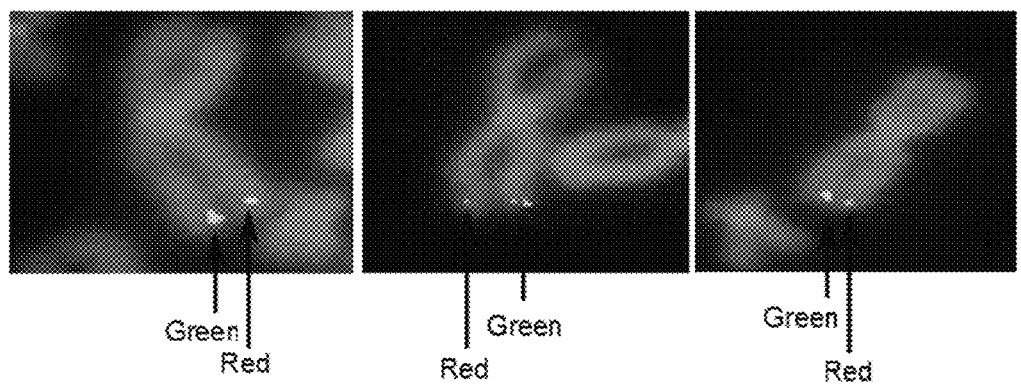
FIG. 3 is a mini-paint labeled with AlexaFluor 488 (green) and with Cy3 (red) using terminal transferase and hybridized to metaphase spreads derived from normal human fibroblasts. Spreads were prepared using the CO-FISH technique. 9 probe sets (green) were designed to hybridize to one chromosome 3 chromatid and one probe set (red) was designed to hybridize to the complementary chromatid.

To demonstrate the feasibility of detecting very small inversions, 10 probe sets, spaced 1 Mb apart were developed to a 10 Mb region on the large 3q contig. The middle probe set of the "mini-paint" was designed either to be oriented along with the other 9 probe sets or to be oriented anti-parallel to the others. The complementary probe set was expected to anneal to the other chromatid if there is NOT an inversion, in effect simulating the pattern of a small inversion. Each probe set consisted of 90 individual oligos. The fluorescent signal derived from the "mini-paint" was located on one chromatid as expected (not shown). When the middle probe set was replaced with the complementary (anti-parallel) probe set, a fluorescent signal from the single probe set appeared on the opposite chromatid. (See FIG. 3).

The development of the "mini-paint" and other applications of simulating a small inversion are important for several reasons. They verify that a single probe set hybridizing to the opposite chromatid, such as after an inversion, can be detected at high frequency (>90%). The complementary probe set labeled a different color serves as a useful developmental tool to verify detection limits of single probe sets in the context of a chromatid paint, but we also observed the single complementary probe set when it was labeled the same color as the "mini-paint", and at equally high frequencies (not shown). Additionally the "mini-paint" concept provides a simple, cost effective platform for diagnostic assays that will allow detection of clinically relevant small inversions. Complementary probe sets could be spaced at desired intervals, and if appropriately spaced could be used as a "cytogenetic ruler". A cytogenetic ruler would be useful in identifying and defining inversion breakpoints.

The foregoing description of the invention has been presented for purposes of illustration and description and is not intended to be exhaustive or to limit the invention to the precise form disclosed, and obviously many modifications and variations are possible in light of the above teaching. The embodiments were chosen and described in order to best explain the principles of the invention and its practical application to thereby enable others skilled in the art to best utilize the invention in various embodiments and with various modifications as are suited to the particular use contemplated. It is intended that the scope of the invention be defined by the claims appended hereto.

The invention claimed is:

1. A kit for detecting inversions in a selected mitotic chromosome, comprising a plurality of non-repetitive probes, wherein each of the probes in the plurality of probes is single-stranded, unique and identical to at least a portion of a target DNA sequence of only one DNA strand of only one chromatid of the chromosome, each of the probes having at least one label and each probe being 20 to 48 nucleotides in length, thereby permitting detection thereof.

2. The kit of claim 1, further comprising reagents suitable for performing the CO-FISH process to generate single-stranded chromatids from the selected mitotic chromosome, comprising 5-bromo-2'-deoxyuridine and Exonuclease III.

3. The kit of claim 2, further comprising reagents suitable for hybridizing the probes to the single-stranded chromatids.

4. The kit of claim 1, wherein the at least one label comprises a fluorescent label.

5. A kit for detecting inversions in a selected mitotic chromosome, comprising a plurality of non-repetitive probes, wherein each of the probes in the plurality of probes is single-stranded, unique and complementary to at least a portion of a target DNA sequence of only one DNA strand of only one chromatid of the chromosome, each of the probes having at least one label and each probe being 20 to 48 nucleotides in length, thereby permitting detection thereof.

6. The kit of claim 5, further comprising reagents adapted to performing the CO-FISH process to generate single-stranded chromatids from the selected mitotic chromosome, comprising 5-bromo-2'-deoxyuridine and Exonuclease III.

7. The kit of claim 6, further comprising reagents suitable for hybridizing the probes to the single-stranded chromatids.

8. The kit of claim 5, wherein the at least one label comprises a fluorescent label.

* * * * *